US007977110B2

(12) United States Patent
Barasch et al.

(10) Patent No.: US 7,977,110 B2
(45) Date of Patent: Jul. 12, 2011

(54) METHOD FOR DISTINGUISHING BETWEEN KIDNEY DYSFUNCTIONS

(75) Inventors: Jonathan Matthew Barasch, New York City, NY (US); Prasad Devarajan, Cincinnati, OH (US); Thomas L. Nickolas, Brooklyn, NY (US)

(73) Assignees: Children's Hospital Medical Center, Cincinnati, OH (US); The Trustees of Columbia University, New York, NY (US)

( * ) Notice: Subject to any disclaimer, the term of this patent is extended or adjusted under 35 U.S.C. 154(b) by 0 days.

(21) Appl. No.: 12/143,769

(22) Filed: Jun. 21, 2008

(65) Prior Publication Data

US 2009/0298047 A1    Dec. 3, 2009

Related U.S. Application Data

(60) Provisional application No. 61/058,068, filed on Jun. 2, 2008.

(51) Int. Cl.
*C12Q 1/25* (2006.01)
*G01N 33/53* (2006.01)
(52) U.S. Cl. ................ 436/96; 435/4; 435/7.9
(58) Field of Classification Search .......... 436/196, 436/96; 435/4, 7.9
See application file for complete search history.

(56) References Cited

U.S. PATENT DOCUMENTS

| 6,136,526 | A | 10/2000 | Venge | |
|---|---|---|---|---|
| 2004/0219603 | A1 | 11/2004 | Devarajan et al. | |
| 2005/0272101 | A1* | 12/2005 | Devarajan et al. | 435/7.9 |
| 2009/0170143 | A1 | 7/2009 | Uttenthal et al. | |

FOREIGN PATENT DOCUMENTS

| WO | WO 2004/005544 | 1/2004 |
|---|---|---|
| WO | WO 2006/066587 | 6/2006 |
| WO | WO 2007/137582 | 12/2007 |
| WO | WO 2007/137584 | 12/2007 |

(Continued)

OTHER PUBLICATIONS

Devarajan, P, Novel biomarkers for the early prediction of acute kidney injury; Cancer Therapy, vol. 3, Sep. 2005, pp. 477-488.

(Continued)

*Primary Examiner* — Vickie Kim
*Assistant Examiner* — Rebecca Fritchman
(74) *Attorney, Agent, or Firm* — Hasse & Nesbitt LLC; Daniel F. Nesbitt

(57) ABSTRACT

A method for distinguishing between kidney dysfunctions in a mammal, including pre-renal azotemia, an acute renal injury that may progress to acute renal failure, and chronic kidney disease, using a urinary or circulating NGAL assay result that is compared to a predetermined NGAL cutoff level, and a single serum or plasma creatinine measurement. Typically the single creatinine measurement cannot distinguish acute renal injury from chronic kidney disease or pre-renal azotemia, a single measurement of urinary NGAL, combined with the single serum or plasma creatinine measurement, has sufficient sensitivity and specificity to distinguish acute renal injury from normal function, prerenal azotemia, and chronic kidney disease and predicts poor inpatient outcomes. Patients admitted to the emergency department of the hospital with any of acute kidney injury, prerenal azotemia, chronic kidney disease, or even normal kidney function, can be evaluated based on the single measurements of urinary or circulating NGAL, and serum or plasma creatinine. Urinary NGAL level is highly predictive of clinical outcomes, including nephrology consultation, dialysis, and admission to the intensive care unit.

17 Claims, 3 Drawing Sheets

FOREIGN PATENT DOCUMENTS

WO    WO 2008/017306    2/2008

OTHER PUBLICATIONS

Kjeldsen, L., et al., Characterization of two ELISAs for NGAL, a newly described lipocalin in human neutrophils, Journal of Immunological Methods 198, Nov. 1996, pp. 155-164.

Matthaeus, T, et al., Acute Ischemic Renal Failure Induces Expression of Neutrophil Gelatinase-Associated Lipocalin and Matrix Metalloproteinase-9 in Damaged Tubuli, Kidney Blood Press Res, vol. 24, Congress of Nephrology, Sep./Oct. 2001, p. 342 (2 pages).

Matthaeus, T, et al., Co-Regulation of Neutrophil Gelatinase-Associated Lipocalin and Matrix Metalloproteinase-9 in the Postischemic Rat Kidney, J Am Soc Nephrol vol. 12, Sep. 2001, Pathophysiology of Renal Disease: Acute Renal Failure, pp. 787A; A4112 (1 page).

Mishra, J, et al., Identification of Neutrophil Gelatinase-Associated Lipocalin as a Novel Early Urinary Biomarker for Ischemic Renal Injury, J Am Soc Nephrol, vol. 14, Oct. 2003, pp. 2534-2543.

Mishra, J, et al., Amelioration of Ischemic Acute Renal Injury by Neutrophil Gelatinase-Associated Lipocalin; J. Am. Soc Nephrol, vol. 15, Dec. 2004, pp. 3073-3082.

Mishra, J, et al., Neutrophil gelatinase-associated lipocalin (NGAL) as a biomarker for acute renal injury after cardiac surgery, The Lancet, vol. 365, Apr. 2, 2005, pp. 1231-1238.

Mishra, J, et al., Neutrophil Gelatinase-Associated Lipocalin: A Novel Early Urinary Biomarker for Cisplatin Nephrotoxicity, Am J Nephrol, vol. 24, May 2004, pp. 307-315.

Ohlsson, S, et al., Increased Ciruculating Levels of Proteinase 3 in Patients with Anti-Neutrophilic Cytoplasmic Autoantibodies-Associated Systemic Vasculitis in Remission, Clin Exp Immunol, vol. 131, Mar. 2003, pp. 528-535.

Bellomo, R, et al., Acute Dialysis Quality Initiative Workgroup. Acute renal failure-definition, outcome measures, animal models, fluid therapy and information technology needs: the Second International Consensus Conference of the Acute Dialysis Quality Initiative (ADQI) Group, Crit Care, vol. 8, 2004; pp. R204-212.

Bonventre, J V, et al., Recent advances in the pathophysiology of ischemic acute renal failure, J Am Soc Nephrol, vol. 14, 2003, pp. 2199-2210.

Chertow, G M, et al., Acute kidney injury, mortality, length of stay, and costs in hospitalized patients, J Am Soc Nephrol, vol. 16, 2005, pp. 3365-3370.

Dent, C L, et al., Plasma neutrophil gelatinase-associated lipocalin predicts acute kidney injury, morbidity and mortality after pediatric cardiac surgery: a prospective uncontrolled cohort study, BioMed Central Ltd, Dec. 2007, http://ccforum.com/content/11/6/R127, (8 pages).

Devarajan, P, et al., The von Hippel-Lindau Gene Product Inhibits Renal Cell Apoptosis via Bcl-2-dependent Pathways, The Journal of Biological Chemistry,vol. 276, No. 44, Nov. 2, 2001, pp. 40599-40605.

Gottlieb, S S, et al., The prognostic importance of different definitions of worsening renal function in congestive heart failure, Journal of Cardiac Failure, vol. 8, No. 3, 2002, pp. 136-141.

Han, W K, et al., Urinary biomarkers in the early diagnosis of acute kidney injury, Kidney International, http://kidney.international.org, 2007, pp. 1-7.

Han, W K, et al., Kidney Injury Molecule-1(KIM-1): A novel biomarker for human renal proximal tubule injury; Kidney International, vol. 62, Jul. 2002, pp. 237-244.

Herget-Rosenthal, S, et al., Early detection of acute renal failure by serum cystatin C, Kidney International, vol. 66, Issue 3, Sep. 2004, pp. 1115-1122.

Hirsch, R, et al., NGAL is an early predictive biomarker of contrast-induced nephropathy in children, Pediatr Nephrol, DOI 10.1007/s00467-007-0601-4, Jul. 2007 (7 pages).

Ichimura, T, et al., Kidney Injury Molecule-1 (KIM-1), a Putative Epithelial Cell Adhesion Molecule Containing a Novel Immunoglobulin Domain, Is Up-regulated in Renal Cells after Injury, The Journal for Biological Chemistry, vol. 273, No. 7, Feb. 13, 1998, pp. 4135-4142.

Kjeldsen, L, et al., Human neutrophil gelatinase-associated lipocalin and homologous proteins in rat and mouse, Biochimica et Biophysica Acta 1482, Feb. 10, 2000, pp. 272-283.

Kjeldsen, L, et al., Isolation and Primary Structure of NGAL, a Novel Protein Associated with Human Neutrophil Gelatinase, The Journal of Biological Chemistry, vol. 268, No. 14, May 15, 1993, pp. 10425-10432.

Lameire, N, et al., Reflections on the definition, classification, and diagnostic evaluation of acute renal failure [Editorial], Current Opinion in Critical Care,vol. 10, 2004, pp. 468-475.

Lassnigg, A, et al., Minimal changes of serum creatinine predict prognosis in patients after cardiothoracic surgery: a prospective cohort study, J Am Soc Nephrol, vol. 15, 2004, pp. 1597-1605.

Liangos, O, et al., Urinary N-acetyl-beta-(D)-glucosaminidase activity and kidney injury molecule-1 level are associated with adverse outcomes in acute renal failure, J Am Soc Nephrol, vol. 18, 2007, pp. 904-912.

Molitoris, B A, et al, Acute renal failure II. Experimental models of acute renal failure: imperfect but indispensable, Am J Physiol Renal Physiol, vol. 278, Jan. 2000, pp. F1-F12.

Mori, J, et al., Endocytic delivery of lipocalin-siderophore-iron complex rescues the kidney from ischemia-reperfusion injury, The Journal of Clinical Investigation, vol. 115, No. 3, Mar. 2005, pp. 610-621.

Muramatsu, Y, et al., Early detection of cysteine rich protein 61 (CYR61, CCNI) in urine following renal ischemic reperfusion injury, Kindney International, vol. 62, Nov. 2002, pp. 1601-1610.

Nickolas, T, et al., A Single Measurement of Urine Neutrophil Gelatinase-Associated Lipocalin Indentifies Acute Kidney Injury at Hospital Presentation and Predicts Poor Outcome, Clinical Nephrology: Acute Kidney Injury: Clinical II, Poster Board No. SU-P0953, Nov. 4, 2007 (1 page).

O'Rourke, et al., Urinary Biomarkers of Renal Failure, unpublished-presentation at poster session, Rio de Janeiro, Brazil, May 27, 2007 (18 pages).

Barasch, J, et al., Biomarkers of Renal Disease, unpublished-presentation at seminar, Berlin, Germany, Jun. 22, 2007 (37 pages).

Smith, G L, et al., Worsening Renal Function: What Is a Clinically Meaningful Change in Creatinine During Hospitalization With Heart Failure?, Journal of Cardiac Failure, vol. 9, No. 1, 2003, pp. 13-25.

Schmidt-Ott, K M, et al., Neutrophil gelatinase-associated lipocalin-mediated iron traffic in kidney epithelia, Current Opinion in Nephrology and Hypertension, 2006, pp. 1-8.

Schmidt-Ott, K M, et al., Duel Action of Neutrophil Gelatinase-Associated Lipocalin, J Am Soc Nephrol, vol. 18, 2007, pp. 407-413.

Supavekin, S, et al., Differential gene expression following early renal ischemia/reperfusion, Kidney International, vol. 63, May 2003, pp. 1714-1724.

Suzuki, M, et al., Neutrophil gelatinase-associated lipcalin as a biomarker of disease activity in pediatric lupus nephritis, Pediatr Nephrol, vol. 23, Mar. 2008, pp. 403-412.

Star, R A, Treatment of acute renal failure, Kidney International, vol. 54, 1998, pp. 1817-1831.

Zanardo, G, et al., Acute Renal Failure in the Patient Undergoing Cardiac Operation, Prevalence, Mortality Rate, and Main Risk Factors, J Thorac Cardiovasc Surg, vol. 107, Issue 6, Jun. 1994, pp. 1489-1495.

Devarajan, P, et al., Gene Expression in Early Ischemic Renal Injury: Clues Toward Pathogenesis, Biomarker Discovery, and Novel Therapeutics, Molecular Genetics and Metabolism, vol. 80, 2003, pp. 365-376.

\* cited by examiner

METHOD FOR DISTINGUISHING BETWEEN KIDNEY DYSFUNCTIONS

CROSS-REFERENCE TO RELATED APPLICATIONS

This application claims the benefit of U.S. Provisional Application No. 61/058,068, filed Jun. 2, 2008, the disclosure of which is incorporated herein by reference.

BACKGROUND

Acute kidney injury (AKI) is a common complication among ambulatory and hospitalized patients, and its incidence has increased by 11% in recent years. It is a rapidly progressive illness that independently predicts excess morbidity and mortality. Twenty percent to 60% of patients with acute kidney injury require dialysis, and mortality rates range from 15% in the community setting to 50% to 80% in the setting of multiorgan failure to more than 80% in the postoperative setting. Less severe forms of acute kidney injury may also result in prolonged hospitalization. These characteristics contrast with those of other kidney diseases, such as chronic kidney disease, which is typified by an insidious decline in renal function and is usually nonprogressive during hospitalization. Acute kidney injury is also distinct from prerenal azotemia, a physiologic response of the kidney to various predisposing factors (volume depletion, diuretic use, renin-angiotensin blockade, congestive heart failure, or cirrhosis of the liver) that promptly resolve on fluid administration, regimen modification, or amelioration of the non-kidney organ malfunction.

It is critical to distinguish acute kidney injury from prerenal azotemia and chronic kidney disease at the time of patient presentation to rapidly manage associated illness. However, the initial measurement of serum creatinine, the standard marker of kidney function, does not distinguish acute kidney injury from prerenal azotemia or chronic kidney disease. In addition, the initial measurement of serum creatinine cannot reflect the extent of injury because its accumulation always lags behind the insult. Even a large decline in glomerular filtration rate (GFR) may manifest as a small change in serum creatinine level, particularly in the initial 48 hours after acute kidney injury before steady-state equilibrium is reached. Serum creatinine may also vary by age, race, sex, muscle mass, metabolism, nutritional status, comorbid conditions, hydration status, and medication use and consequently may not increase in proportion to the severity of the injury. As a result, the diagnosis of acute kidney injury currently requires measuring serum creatinine repeatedly and delaying maneuvers to prevent ongoing kidney damage, such as stopping use of nonsteroidal anti-inflammatory drugs, adjusting medication dosages, or correcting hemodynamic status. Even elevations of serum creatinine level that do not meet established criteria for acute kidney injury are associated with excess mortality, prolonged hospitalization, functional decline, and elevated financial costs, which highlights the insensitivity of serum creatinine measurement as a diagnostic test. These limitations in the use of serum creatinine provide the rationale for the discovery of kidney proteins that are expressed at the onset of injury and are more sensitive and specific for the diagnosis of acute injury than current diagnostic tests.

Neutrophil gelatinase-associated lipocalin (NGAL), also known as lipocalin-2, siderocalin, and 24P3', is secreted into the urine by the thick ascending limb of Henle and collecting ducts of the kidney (See Mishra J et al., J Am Soc Nephrol. 2003; 14:2534-43, and Schmidt-Ott K M, et al., J Am Soc Nephrol. 2007; 18:407-13, the disclosures of which are incorporated herein by reference. At these sites, NGAL is likely to play a critical role in host defense by chelating iron-siderophore complexes that enhance microbial growth or mediate oxidative damage. In some segments of the nephron, NGAL may also recycle the iron complexes by endocytosis. Urinary NGAL is expressed in proportion to the degree of acute injury, whereas in chronic kidney disease, urinary NGAL is expressed in patients with progressive but not stable kidney failure. Volume depletion or diuretics do not increase urinary NGAL levels in mice, again reflecting the specificity of NGAL for ongoing tubular damage. These observations suggest not only that urinary NGAL detects acute kidney injury but also that its degree of expression might distinguish among acute kidney injury, prerenal azotemia, and chronic kidney disease. In addition, because NGAL is detectable before the accumulation of serum creatinine, NGAL might be used to diagnose acute kidney injury at patient presentation even when changes in serum creatinine level are incipient.

SUMMARY OF THE INVENTION

The present invention provides a method for distinguishing between kidney dysfunctions in a mammal, comprising the steps of: determining the level of creatinine in an isolated serum or plasma sample from a blood sample obtained from the mammal to obtain a creatinine assay result, determining the level of NGAL in a urine sample obtained from the mammal, to obtain a urinary NGAL assay result, comparing the creatinine assay result against a creatinine cutoff level, wherein a creatinine assay result above the creatinine cutoff level indicates the mammal has a kidney dysfunction selected from the group consisting of pre-renal azotemia, an acute renal injury that may progress to acute renal failure, or which predisposes the mammal to acute renal failure, and chronic kidney disease; and comparing the urinary NGAL assay result against a urine NGAL cutoff level, wherein a urinary NGAL result above the urine NGAL cutoff level indicates the mammal has an acute renal injury that may progress to acute renal failure.

The present invention provides a method for distinguishing between kidney dysfunctions in a mammal, comprising the steps of: determining the level of creatinine in an isolated serum or plasma sample from a blood sample obtained from the mammal to obtain a creatinine assay result, determining the level of NGAL in the isolated serum or plasma sample from the blood sample to obtain a circulatory NGAL assay result, comparing the creatinine assay result against a creatinine cutoff level, wherein a creatinine result above the creatinine cutoff level indicates the mammal has a kidney dysfunction selected from the group consisting of pre-renal azotemia, an acute renal injury that may progress to acute renal failure, or which predisposes the mammal to acute renal failure, and chronic kidney disease; and comparing the circulating NGAL assay result against a circulating NGAL cutoff level, wherein a circulating NGAL assay result above the circulating NGAL cutoff level indicates the mammal has an acute renal injury that may progress to acute renal failure.

The present invention also relates to a method for distinguishing between kidney dysfunctions in a mammal, including pre-renal azotemia, an acute renal injury that may progress to acute renal failure, and chronic kidney disease, using a urinary or circulating NGAL assay result that is compared to a predetermined NGAL cutoff level, and a single serum or plasma creatinine measurement. Typically the single creatinine measurement cannot distinguish acute renal injury from chronic kidney disease or pre-renal azotemia, a single measurement of urinary NGAL, combined with the single serum or plasma creatinine measurement, has sufficient sensitivity and specificity to distinguish acute renal injury from normal function, prerenal azotemia, and chronic kidney disease and predicts poor inpatient outcomes. Patients admitted to the emergency department of the hospital with any of acute kidney injury, prerenal azotemia, chronic kidney disease, or even normal kidney function, can be evaluated based on the single measurements of urinary or circulating NGAL, and serum or plasma creatinine. Urinary NGAL level is highly predictive of clinical outcomes, including nephrology consultation, dialysis, and admission to the intensive care unit.

Typically the renal injury and function status of the mammal is unknown, upon presentation of the mammal as a patient at a medical facility, including a hospital, emergency room, or clinic. The renal injury and function can include the renal injury or function condition of the mammal. Also typically, the renal injury and function status is not obvious or readily predictable by medical personnel. Also typically, the circumstances or events within the last 24-48 hours preceding the patient's presentation to the hospital, emergency room, or clinic are also unknown. Nevertheless, a prompt and reliable diagnosis of the renal injury of the patient is essential.

The method above is typically sensitive, selective, and rapid. Urinary or circulating NGAL level is a better predictor of the need for nephrology consultation, dialysis, intensive care unit (ICU) admission, and death, than conventional renal injury or function markers such as creatinine, and other emerging biomarkers of acute kidney injury.

The method of distinguishing between kidney dysfunctions in a mammal can include distinguishing from between pre-renal azotemia, an acute renal injury that may progress to acute renal failure (ARF), or which predisposes the mammal to acute renal failure, and chronic kidney disease, as well as normal or healthy kidney status or function, and mild or sub-clinical acute renal injuries that do not progress to ARF. The method of distinguishing between kidney dysfunctions in a mammal can include distinguishing from between pre-renal azotemia and an acute renal injury that may progress to acute renal failure.

The mammal can be a human.

The sampling of either urine or blood from the mammal can be taken by a physician, technician, or other medical personal. The sampling can take place at any facility, and at anytime, though typically at a hospital, clinic, emergency medical unit or physician's office, and typically at the time of admission of the mammal to the facility.

The sampling of blood is typically taken by well known means, including the drawing of blood from the circulating system with a needle into a syringe, ampule or other container. The sampling of urine is typically taken by well known means, including the use of a container to capture a portion of stream of urine, or via a catheter.

The quantity of urine that can be taken that can yield a reliable urinary NGAL assay result is as little as about 1 µl to about 1 ml, or more. The urine sample can be processed by well known means, such as centrifugation, or can be unprocessed or "as-is" for the NGAL assay.

The isolating of a serum sample or a plasma sample from the blood sample is accomplished by well known means. The urine sample can be used as taken as an unprocessed urine sample, or can be processed by well known means, including centrifugation to obtain a supernatant.

The level of creatinine in the isolated serum or plasma sample from the blood sample is assayed by well known means. The level of creatinine in the isolated serum or plasma sample is typically measured and identified as a creatinine assay result in units of micromoles per liter of isolated sample (µmole/L) or in milligram per deciliter of isolated sample (mg/dL). The level of NGAL in the urine sample or in an isolated serum or plasma sample, can be obtained by well known means, and is typically measured and identified as a urinary NGAL assay result in units of nanograms of NGAL per milliliter of urine sample (ng/ml urine, or equivalent units) or nanograms of NGAL per milligram of urine creatinine in the urine sample (ng/mg ucr, or equivalent units), as an internal standard. Conversions of urinary NGAL level in ng/mg ucr to ng/ml urine, are common and generally constant. In the hospital setting, the ng/ml urine unit are typically used.

The creatinine cutoff level (a predetermined level of creatinine in an isolated plasma or serum sample) is typically determined by empirical and historical data on a large number of subjects having the same kidney dysfunction, using statistical analysis to identify a cutoff level with the selectivity and specificity to distinguish between the different kidney dysfunctions.

The step of comparing the urinary NGAL assay result, the circulating NGAL result or the creatinine assay result with an appropriate cutoff value can be done by visual comparison, or an automatic comparison performed by a computer, an instrument or other apparatus.

Mammals identified as having an acute renal injury that may progress to acute renal failure, are typically subjected subsequently to a nephrologic consultation, an admission into an intensive care unit, or the initiation of kidney dialysis.

The urinary NGAL cutoff level, above which the mammal is determined to have an acute renal injury that may progress to acute renal failure (ARF), is typically about or above 75 ng/mg ucr, or about or above 85 ng/mg ucr, or about or above 100 ng/mg ucr, or about or above 110 ng/mg ucr, or about or above 120 ng/mg ucr, or about or above 130 ng/mg ucr, or about or above 140 ng/mg ucr, or about or above 150 ng/mg ucr. Alternatively, the urinary NGAL cutoff level, above which the mammal is determined to have an acute renal injury that may progress to ARF, is typically about or above 75 ng/ml urine, or about or above 100 ng/ml urine, or about or above 125 ng/ml urine, or about or above 150 ng/ml urine, or about or above 200 ng/ml urine, or about or above 250 ng/ml urine, or about or above 300 ng/ml urine, or about or above 350 ng/ml urine. The circulating NGAL cutoff level, above which the mammal is determined to have an acute renal injury that may progress to ARF, is typically about or above 40 ng/ml serum (* indicating an equivalent level of NGAL/ml plasma), or about or above 50 ng/ml serum*, or about or above 65 ng/ml serum*, or about or above 75 ng/ml serum*, or about or above 90 ng/ml serum*, or about or above 100 ng/ml serum*, or about or above 125 ng/ml serum*, or about of above 150 ng/ml serum*. The specific urinary or circulating NGAL cutoff level can be selected, factoring in the specific assay method selected for use.

Alternatively, the urinary or circulating NGAL cutoff level is at least 2-fold or more, or at least 3-fold or more, or at least 4-fold or more, or at least 5-fold or more, or at least 6-fold or more, or at least 7-fold or more, or at least 8-fold or more, or at least 9-fold or more, or at least 10-fold or more, the level of NGAL in the urine sample presented by normal, healthy mammals who are not experiencing any acute kidney injury.

Typically, the mammal (a human or animal) enters the hospital, emergency room, or clinic with an unknown near-term (within the last 24-48 hours) injury history, where the time of the onset or start of any acute or chronic renal injury, as well as the type of injury (for example, trauma, ischemia, nephrotoxic, and others) are unknown to the medical personnel of the hospital, emergency room, or clinic. The prior conditions of the patient and injury are either unknown or not easily confirmed. Meanwhile, a reliable diagnosis of the patient's renal injury status and function are essential for the prescribing of proper care to the patient and to the patient's outcome. On the basis of the urinary or circulating NGAL assay results and the serum or plasma creatinine results, the trained clinician or physician can evaluate the renal injury status and the renal function status of the patient.

In one embodiment of the invention, the determination of the level or quantity of serum or plasma creatinine upon admission to a hospital may show a normal level of creatinine, typical of normal, healthy patients. Nevertheless, that patient may have recently suffered a serious acute renal injury (such as an acute ischemic renal or nephrotoxic injury) which has not yet resulted in a decline in kidney function, but can or does progress in the next several hours (12-24 hours) or even days (1-3 days) into acute renal failure as a result of the latent injury. The measurement of NGAL in the urine or isolated plasma or serum sample can detect the significantly elevated level of NGAL (that is, above the NGAL cutoff level) that identifies the patient as being at risk of progressing to acute renal failure, over the next several hours or days, even while the patient's current kidney function is normal and serum creatinine levels are low and normal.

The comparison of isolated creatinine assay result and the urinary NGAL assay result can also be used to estimate the timing of onset of an event that caused the AKI, or the severity of the acute injury to the kidney, since the onset of the appearance of urinary NGAL is essentially immediate and real-time, while the decline in renal function as a result of the acute injury can be delayed in time, from between 12 and 48 hours, or more.

Typically, in an emergency room setting, the urine and/or blood samples are obtained from the mammal within 2 hours or less, more typically within 1 hour or less, and more typically within 30 minutes or less. Typically the urine and blood samples are taken at the same time.

Typically, the assays to measure NGAL and creatinine are taken immediately or very soon after the samples themselves are taken from the mammal. In many hospital or emergency settings involving suspected renal dysfunction, time is essential. The analysis of the level of NGAL and/or creatinine in the obtained urine sample or the obtained blood sample is typically completed and the result produced within about 6 hours or less, more typically within about 4 hours or less, more typically within about 3 hours or less, more typically within about 2 hours or less, more typically within about 1 hour or less, and more typically within about 30 minutes or less.

Urinary NGAL assay results can be obtained by known quantitative (for example, an enzyme linked immunosorbent assay (ELISA)) or qualitative means (for example, a western blot, which can detect and produce a result indicating a significantly elevated level of NGAL). Typically, the assay provides for contacting the urine sample with an antibody for NGAL to allow formation of a complex of the antibody (also called the capture antibody) and NGAL, and detecting the antibody-NGAL complex. A competitive enzyme linked immunosorbent assay (ELISA) kit for determining the level or quantity of NGAL in the urine sample is preferred. The method for detecting the complex of NGAL and the primary antibody can include the steps of: separating any unbound material of the urine sample from the capture antibody-NGAL complex; contacting the capture antibody-NGAL complex with a second antibody for detecting NGAL, to allow formation of a complex between the NGAL and the second antibody; separating any unbound second antibody from NGAL-second antibody complex; and detecting the second antibody of the NGAL-second antibody complex.

Plasma or serum NGAL assay results can be obtained in a similar method as for the urinary NGAL assay, using a serum or plasma sample isolated from the blood sample.

The acute kidney injury can result from any type of event described hereinafter, including all types of ischemic and nephrotoxic injuries. The nephrotoxin can be exogenous, such as a pharmaceutical, a drug, a medicine, or any other type of commonly confronted toxins, including antibiotics, anti-inflammatory agents, radio-contrast agents, and chemotherapeutic agents. The nephrotoxin can be endogenous, such as hemoglobin (for example, due to hemolysis), myoglobin (for example, due to rhabdomyolysis) or uric acid (for example, due to tumor lysis). The ischemic injury can result from any stoppage or slowing of blood flow to the kidney or other major organ of the body, and can include surgeries of all types, kidney transplantation, stroke, trauma, and severe stages of sepsis and dehydration.

The acute kidney injury can range from a mild or subclinical injury, which elevates the level of NGAL in the urine sample but below the urinary NGAL cutoff level, to a more serious acute kidney injury, which elevates the level of NGAL in the urine sample above the urinary NGAL cutoff level, and that puts the mammal at a significant risk of progressing with time to acute renal failure (ARF).

In a typical emergency room setting, the serum or plasma creatinine remains as an early and standard biomarker. The renal status of most patients entering an emergency room is unknown. Typically, an elevated level of serum creatinine can indicate any one or all of chronic kidney disease, pre-renal azotemia, and an acute kidney injury that has occurred an indeterminate time before entering the emergency room. As described in US patent application publication 2004-0219603, Devarajan et al, the disclosure of which is incorporated herein by reference, the onset of injury to the renal tubular cells and the appearance of NGAL in the urine well precedes the decline in renal function resulting from the renal injury, which is manifest in a rise in serum creatinine. Similarly, as described in US patent application publication 2005-0272101, Devarajan et al, the disclosure of which is incorporated herein by reference, the onset of injury to the renal tubular cells and the appearance of NGAL in the plasma or serum isolated from a blood sample well precedes the decline in renal function resulting from the renal injury, manifest in the rise in serum creatinine. Consequently, a determination of the level of serum creatinine can indicate that the patient has chronic renal disease, pre-renal azotemia, or an acute kidney injury that can progress to acute renal failure. In the case of an acute kidney injury that can progress to acute renal failure, it is important that the patient receive a nephrology consultation, admission into intensive care, or the initiation of dialysis, or a combination thereof, depending upon the level of urinary NGAL as an indication of the severity of the acute kidney injury.

DETAILED DESCRIPTION AND EXAMPLE OF THE INVENTION

Definitions

Figure 1:
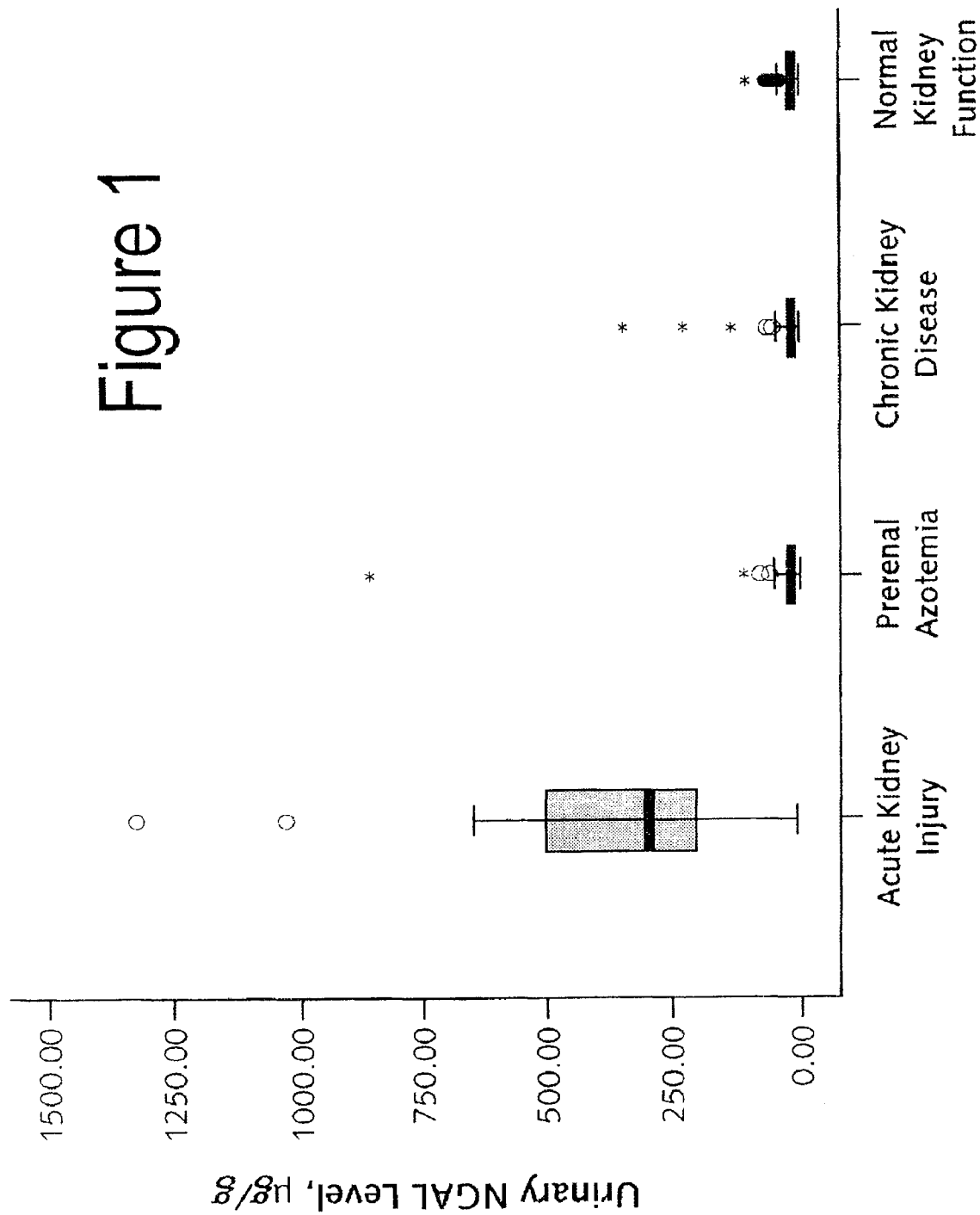
FIG. 1 shows a box plot of urinary neutrophil gelatinase-associated lipocalin (NGAL) and serum creatinine levels, for different diagnostic groups, wherein patients with acute kidney injury had markedly elevated mean urinary NGAL levels compared with patients who had other forms of kidney dysfunction.

"Normal kidney function" is defined as a baseline estimated GFR greater than 60 mL/min per 1.73 m2 and no transient or sustained increases in serum creatinine level or decreases in estimated GFR.

"Nonprogressive chronic kidney disease" is defined as a sustained and unchanging (defined as <25% change from baseline) increase in serum creatinine level that met our criteria for altered kidney function and persisted for more than 3 months, reflecting a stably reduced estimated GFR of less than 60 mL/min per 1.73 m2.

"Presumptive nonprogressive chronic kidney disease" is defined, in the absence of retrospective data, as a sustained elevated serum creatinine level that did not change during hospitalization and reflected a stable estimated GFR of less than 60 ml/min per 1.73 m2 despite volume resuscitation.

"Pre-renal azotemia" is defined as a new-onset increase in serum creatinine level that satisfied a criteria for altered kidney function and either resolved within 3 days with treatment aimed at restoring perfusion, such as intravenous volume repletion or discontinuation of diuretics (in the setting of historical and laboratory data suggesting decreased renal perfusion), or was accompanied by fractional excretion of sodium less than 1% at presentation. Pre-renal azotemia is caused by an inadequate supply of blood to the kidneys, and is also referred to as effective volume depletion.

"Acute kidney injury" was defined as a new-onset 1.5-fold increase in serum creatinine level or a 25% decrease in estimated GFR from baseline values that satisfied minimal RIFLE (risk for kidney dysfunction, injury to the kidney, failure of kidney function, loss of kidney function, and end-stage kidney disease) criteria for serum creatinine and GFR that was sustained for at least 3 days despite volume resuscitation. The RIFLE criteria provide a meaningful way to stratify patients at different stages of kidney failure on the basis of severity (risk, injury, failure) and outcome (loss and end-stage disease) (Appendix Table, available at www.annals.org).

A "renal injury", including an acute renal injury including an acute ischemic renal injury and a nephrotoxic injury, and a chronic renal injury, is typically an injury to the tubules of the kidney, including the distal tubules and distal tubule cells, and the proximal tubules.

Because of the diagnostic ambiguities that can occur with current tests at patient presentation to a hospital, clinic, or other medical facility, a prospective cohort study at an inner-city emergency department was studied to determine the accuracy of urinary NGAL assay results to identify acute kidney injury that can progress to ARF. Each participant's hospital course was followed to determine the relationship among the presenting level of NGAL and other urinary proteins, serum creatinine level, and patient outcome. A single measurement of urinary or circulating NGAL is superior to conventional and other biomarkers in predicting acute kidney injury and its comorbid conditions, and a combination of a measurement of urinary or circulating NGAL with a measurement of circulating (serum or plasma) creatinine can distinguish an acute kidney injury that can progress to ARF, from other renal dysfunctions including prerenal azotemia and chronic kidney injury, which are kidney dysfunctions that do not require the same degree, urgency and immediacy of medical attention and care as an acute kidney injury.

Urinary NGAL concentration, including the mean urinary NGAL concentration, is significantly elevated in patients with acute kidney injury. Patients with prerenal azotemia, nonprogressive chronic kidney disease, or normal kidney function had uniformly low urinary NGAL, less than the urinary NGAL cutoff level.

Statistically, urinary NGAL level (or quantity) strongly correlates with acute kidney injury, compared to levels of serum creatinine or other renal biomarkers. A low or subjectively negative urinary NGAL level (or quantity), well below the urinary NGAL cutoff value, strongly correlates with the absence of acute kidney injury.

Studies in children and adults have previously shown that urinary NGAL is rapidly and massively expressed in well-defined cases of acute kidney injury. For example, in a prospective study of children receiving cardiopulmonary bypass, urinary NGAL levels greater than 50 μg/L at 2 hours after surgery had 100% sensitivity and 98% specificity for the subsequent diagnosis of acute kidney injury (AUC, 99.8%) that may progress to ARF. In contrast, even 1 to 3 days after surgery, acute kidney injury could not be diagnosed by using criteria based on serum creatinine level (such as a 50% increase). These findings have been confirmed in a prospective study of adults who had cardiac surgery, in whom the urinary NGAL level increased rapidly after surgery (postoperative AUC, 74% at 3 hours and 80% at 18 hours). Similarly, in a prospective study of children receiving intensive care, urinary NGAL increased 48 hours before a diagnosis based on serum creatinine level was possible. Neutrophil gelatinase-associated lipocalin has also been evaluated as a biomarker of acute injury in kidney transplantation, and multiple studies have shown a significant correlation between NGAL levels and delayed graft function. In each of these studies, patients were intentionally chosen to eliminate comorbid conditions and confounding variables and to test a specific type of injury with unequivocal timing (for example, after surgery).

In contrast to these studies, urinary or circulating NGAL level identifies and distinguishes acute kidney injury in a broad patient sample with different and often unknown mechanisms and status of renal injury. In addition, urinary or circulating NGAL level remains highly diagnostic even when the timing of injury was unknown, making NGAL a diagnostic of kidney disease for many clinical presentations.

Interest in identifying kidney proteins that permit risk assessment, early diagnosis of injury, or surveillance of acute kidney function is intense, and NGAL alone or as a member in a panel of biomarkers is probably required. Other biomarker candidates include interleukin-18, a proinflammatory cytokine that is induced in the proximal tubule and whose levels peak 6 to 12 hours after acute renal injury or disease but not chronic disease or prerenal azotemia. The urinary interleukin-18 level can increase 24 hours before the serum creatinine level in acute renal ischemia (AUC, 73%). The serum cystatin C level also anticipates acute kidney injury (AUC, 97%) 1 to 2 days before the serum creatinine level (AUC, 82%), and an increased urinary cystatin C level has predicted the need for dialysis (AUC, 75%) earlier than serum creatinine. However, in a study of 202 patients, cystatin C did not outperform serum creatinine in the diagnosis of acute injury or prediction of clinical outcomes. Urinary levels of kidney injury molecule-1 (KIM-1), derived from the proximal tubule, can distinguish ischemic injury from prerenal azotemia and chronic kidney disease. In a case-control study of 20 patients with acute kidney injury and 20 control patients, kidney injury molecule-1 levels peaked 12 hours after injury (AUC, 83%) and predicted a combined end point of dialysis or death in hospitalized patients (AUC, 61%). In a cross-sectional study of 20 children, NAG identified acute kidney injury 12 hours after insult (AUC, 69%). Urinary α1-microglobuline increased 8-fold after tubular damage, and patients nearing a requirement for dialysis after acute injury also had increased urinary α1-microglobulin levels. α1-Acid glycoprotein increased 5-fold within 2 hours of cardiopulmonary surgery in patients who developed acute kidney injury.

Methods

Laboratory Measurements

Urine samples are centrifuged at 12,000 rpm for 10 minutes and stored the supernatants at −80° C. Urinary NGAL (10 μL) was quantified by immunoblots with nonreducing 4% to 20% gradient polyacrylamide gels (Bio-Rad Laboratories, Hercules, Calif.) and monoclonal (1:1000; Antibody Shop, BioPorto Diagnostics, Gentofte, Denmark) or rabbit polyclonal antibodies together with standards (0.2 to 10 ng) of human recombinant NGAL protein. (Optionally, urinary NGAL can be determined by measurement of an unprocessed urine sample.) The measurement was reproducible to 0.4 ng/lane. We selected the immunoblotting procedure (run time, approximately 10 hours) instead of commercially available enzyme-linked immunosorbent assays (run time, approximately 4 hours) to authenticate monomeric NGAL. Urinary N-acetyl-β-D-glucosaminidase (NAG) activity was assayed by using an N-acetyl-β-D-glucosaminidase kit (Roche Diagnostics, Mannheim, Germany), and α1-microglobulin and α1-acid glycoprotein were assayed by immunonephelometry with the Dade Behring BN ProSpec System (Dade Behring, Marburg, Germany) at Cincinnati Children's Hospital, Cincinnati, Ohio; the intra-assay and interassay variation coefficients were less than 5%. Urinary creatinine was measured by using a QuantiChrom Creatinine Assay Kit (BioAssay Systems, Hayward, Calif.). Urinary sodium was quantified by using the Olympus AU2700 analyzer (Olympus Imaging America, Center Valley, Pa.). Urinary proteins were measured in absolute terms and normalized to urinary creatinine, resulting in similar test characteristics (data not shown). Serum creatinine, the reference standard, was measured in the Columbia University Medical Center Core Laboratory by using the Jaffe reaction.

Statistical Analysis

We used SPSS, version 13.0 (SPSS, Chicago, Ill.), and SAS, version 9.1 (SAS Institute, Cary, N.C.). Continuous variables were compared between groups by using analysis of variance and categorical variables by using chi-square tests, rejecting the null hypothesis at $P<0.05$. Data are represented as the mean (SD). To determine the diagnostic test characteristics, conventional receiver-operating characteristic (ROC) curves were generated and a nonparametric approach was used for correlated ROC curves to compare discriminatory power. Biomarker cutoff levels were derived from ROC analysis to maximize sensitivity and specificity. Likelihood ratios and 95% CIs for each biomarker were also determined. The McNemar test was used to measure the association of each biomarker with defined clinical outcomes of nephrology consultation, ICU admission, initiation of hemodialysis, and inpatient death. To determine the association of biomarkers, demographic variables (age, sex, and race), comorbid conditions (diabetes, hypertension, congestive heart failure and cirrhosis) and laboratory values (blood urea nitrogen level and leukocyte count) with any of the 4 clinical outcomes, univariate logistic regression analysis were performed. The parameters were included that were significantly associated with the combined clinical outcome in a multiple logistic regression model to identify the independent variables most associated with combined clinical outcomes, which was the dependent variable. Because urinary sodium concentrations were not measured for patients with normal kidney function, fractional excretion of sodium was tested to discriminate acute kidney injury from patients with other types of kidney dysfunction.

EXAMPLE

A study was conducted with recruited consecutive patients 18 years and older who visited the Columbia University Medical Center emergency department between 6 a.m. and 12 a.m from March to August 2007. We obtained the first sample of donated urine and blood. We excluded 17 patients who were receiving hemodialysis and 230 patients without subsequent creatinine measurements from further analysis, as shown in FIG. 1.

Altered kidney function is defined by age- and sex-based criteria: men and women between 18 and 50 years of age with a serum creatinine level greater than 106 μmol/L (>1.2 mg/dL), men older than 50 years with a level greater than 88.4 μmol/L (>1.0 mg/dL), and women with a level greater than 70 μmol/L (>0.8 mg/dL). We estimated GFR by using the Modification of Diet and Renal Disease formula, described in Levey AS et al., Ann Intern Med. 1999; 130:461-70, the disclosure of which is incorporated herein by reference.

Baseline kidney function was defined for 509 patients from a retrospective analysis of serum creatinine, medical history, and demographic characteristics recorded in the Columbia University Medical Center electronic records for the 1 to 12 months before admission. A prospective analysis of kidney function after hospital admission consisted of daily serum chemistry studies and renal ultrasonography. On the basis of the retrospective and prospective studies, a coordinator and an internist who were blinded to the experimental measurements independently assigned patients to 1 of 4 diagnostic categories (normal kidney function, nonprogressive chronic kidney disease, prerenal azotemia, or acute kidney injury); a nephrologist adjudicated the 24 cases of disagreement.

"Normal kidney function" was defined as a baseline estimated GFR greater than 60 mL/min per 1.73 m2 and no transient or sustained increases in serum creatinine level or decreases in estimated GFR during the patient's stay in the hospital.

"Nonprogressive chronic kidney disease" was defined as a sustained and unchanging (defined as <25% change from baseline) increase in serum creatinine level that met our criteria for altered kidney function and persisted for more than 3 months before hospitalization, reflecting a stably reduced estimated GFR of less than 60 mL/min per 1.73 m2 that is consistent with the National Kidney Foundation's Kidney Disease Outcomes Quality Initiative definition of chronic kidney disease. In the absence of retrospective data, presumptive nonprogressive chronic kidney disease was diagnosed if patients had a sustained elevated serum creatinine level that did not change during hospitalization and reflected a stable estimated GFR of less than 60 ml/min per 1.73 m2 despite volume resuscitation.

"Prerenal azotemia" was defined as a new-onset increase in serum creatinine level that satisfied a criteria for altered kidney function and either resolved within 3 days with treatment aimed at restoring perfusion, such as intravenous volume repletion or discontinuation of diuretics (in the setting of historical and laboratory data suggesting decreased renal perfusion), or was accompanied by fractional excretion of sodium less than 1% at presentation.

"Acute kidney injury" was defined as a new-onset 1.5-fold increase in serum creatinine level or a 25% decrease in estimated GFR from baseline values that satisfied minimal RIFLE (risk for kidney dysfunction, injury to the kidney, failure of kidney function, loss of kidney function, and end-stage kidney disease) criteria for serum creatinine and GFR that was sustained for at least 3 days despite volume resuscitation. The RIFLE criteria provide a meaningful way to stratify patients at different stages of kidney failure on the basis of severity (risk, injury, failure) and outcome (loss and end-stage disease) (Appendix Table, available at www.annals.org).

Patient outcomes (nephrology consultation, intensive care admission, dialysis initiation, mortality) were identified prospectively from electronic medical records.

Baseline Characteristics

We received urine and blood samples for biomarker measurements from 882 adults presenting to the emergency department for hospital admission. From these, we excluded 247 persons, as shown in FIG. 1. We prospectively tracked kidney function in the remaining 635 patients by subsequent measurements of serum creatinine level while they were in the hospital. Approximately one half of the patients were male and one quarter were black. Mean age was 60.1 years (SD, 0.7). Thirty patients met our criteria for acute kidney injury (4.7%), 88 patients had prerenal azotemia (13.8%), 106 patients had nonprogressive chronic kidney disease (16.6%), and 411 patients (64.7%) had normal kidney function, as shown in Table 2. The primary causes of acute kidney injury included cardiogenic shock (40%), urinary obstruction diagnosed by renal ultrasonography, (16.7%), multiple myeloma (10%), sepsis (6.7%) hypertensive emergency (6.7%), nephrotoxicity from nonsteroidal antiinflammatory drugs (6.7%), lupus nephritis (3.3%), biopsyconfirmed acute interstitial nephritis (3.3%), glomerulonephritis (3.3%), and rhabdomyolysis (3.3%). Previous baseline creatinine data were available for 509 (80%) patients, including 26 (87%) patients with acute kidney injury, 74 (84%) patients with prerenal azotemia, 94 (89%) patients with stable chronic kidney disease, and 315 (76%) patients with normal kidney function. Patients with acute kidney injury were similar to patients with chronic kidney disease in sex distribution, but they were younger and more than half were black. They also had the highest mean serum creatinine at baseline and presentation and the greatest mean increase in serum creatinine (when baseline data were available for comparison). In addition, patients with acute kidney injury had the highest levels of blood urea nitrogen and urinary leukocytes and the highest fractional excretion of sodium.

The mean urinary NGAL concentration was significantly elevated in patients with acute kidney injury, as shown in Table 1, whereas patients with prerenal azotemia, nonprogressive chronic kidney disease, or normal kidney function had uniformly low urinary NGAL, as shown in FIG. 1. Mean NAG, α1-microglobulin, and α1-acid glycoprotein levels showed the same pattern of association, as shown in Table 1.

Figure 2:
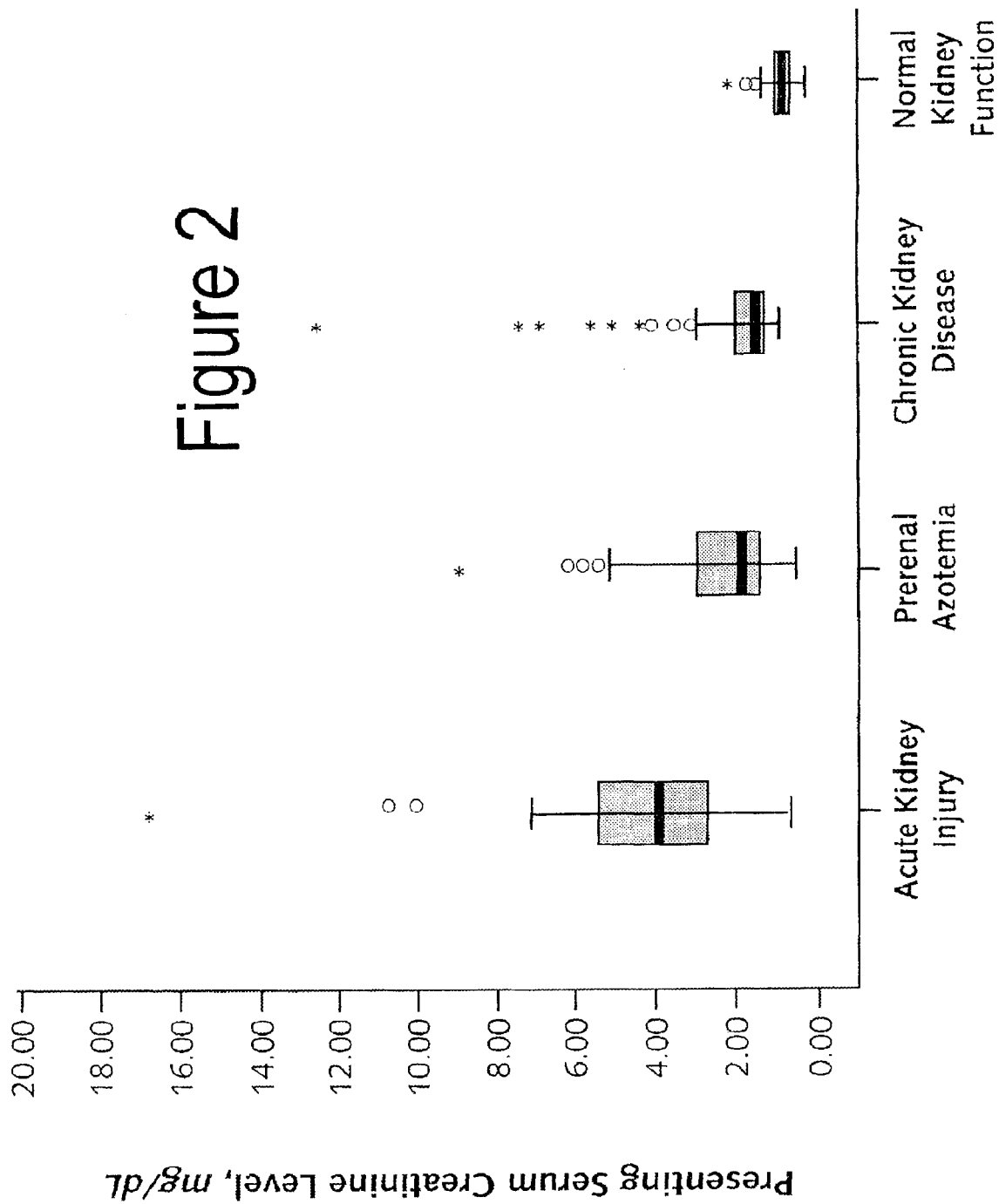
FIG. 2 shows another box plot of urinary neutrophil gelatinase-associated lipocalin (NGAL) and serum creatinine levels, for the different diagnostic groups, wherein the patients with acute kidney injury had significantly elevated mean serum creatinine levels compared with patients who had other forms of kidney dysfunction, but values overlapped among the different categories of kidney function.

To determine whether NGAL could predict acute kidney injury better than other biomarkers, we performed an ROC analysis. Table 2 shows the area under the ROC curve (AUC) for each biomarker and sensitivities, specificities, and positive and negative likelihood ratios. Whereas the AUC for NGAL did not significantly differ from that for serum creatinine (P=0.60) or α1-microglobulin (P=0.100), the AUC for NGAL was significantly higher than that for α1-acid glycoprotein (P=0.003) or NAG (P value<0.001). At either of 2 cutoff values (>85 μg/g creatinine or >130 μg/g creatinine), a positive urinary NGAL level had a stronger correlation with acute kidney injury than levels of serum creatinine or other biomarkers. A negative urinary NGAL level was also highly associated with the absence of acute kidney injury at both cutoff values. FIG. 2 shows box plots for urinary NGAL and serum creatinine measurements stratified by each type of kidney dysfunction. Although NGAL values overlapped very little among patient categories, serum creatinine values overlapped substantially.

Figure 3:
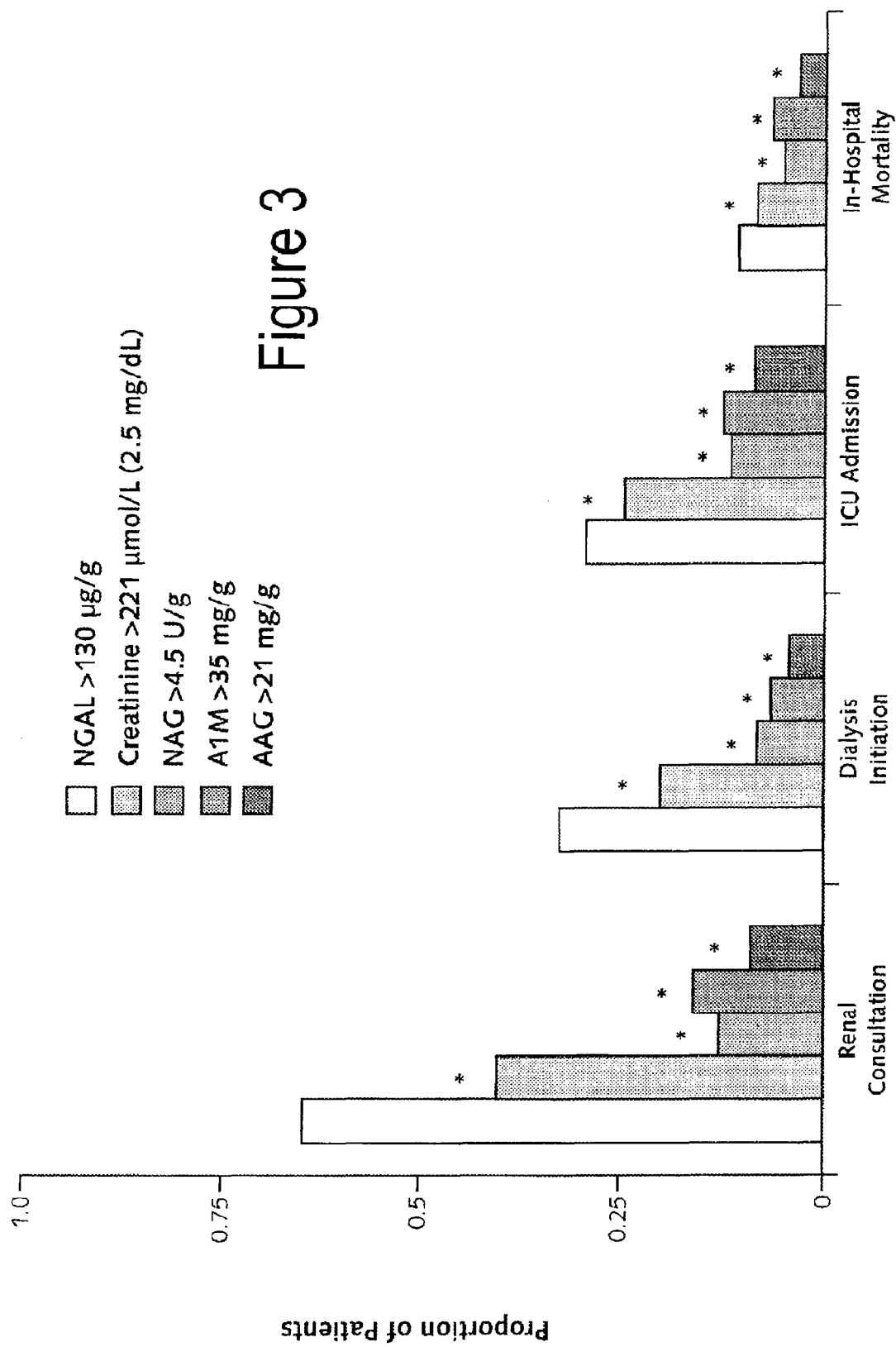
FIG. 3 shows the proportion of patients with biomarker levels above the selected cutoffs, versus clinical outcome. The total number of patients whose levels were above the cutoff was 66 for creatinine, 31 for neutrophil gelatinase-associated lipocalin (NGAL), 133 for N-acetyl-β-D glucosaminidase (NAG), 143 for α1-microglobulin (AIM), and 294 for α1-acid glycoprotein (AAG). *P<0.001 compared with NGAL. The measurements of the biomarkers are normalized per gram of urine creatinine.

To determine the association between clinical outcomes and biomarkers, we used ROC analysis to choose cutoffs that maximized both sensitivity and specificity for acute kidney injury, as shown in FIG. 3. Of the 31 patients with a urinary NGAL level of at least 130 μg/g creatinine on presentation to the emergency department, 64.5% required nephrology consultation, 32.3% required initiation of dialysis, 29.3% required ICU admission, and 9.7% died during hospitalization. A urinary NGAL level greater than 130 μg/g creatinine identified more patients who received nephrology consultation, dialysis initiation, or ICU admission than did other biomarkers (P<0.001 for NGAL compared with all biomarkers).

The total number of patients whose levels were above the cutoff was 66 for creatinine, 133 for N-acetyl-β-D glucosaminidase (NAG), 143 for α1-microglobulin (AIM), and 294 for α1-acid glycoprotein (AAG).

We used univariate logistic regression to evaluate the association of conventional and novel biomarkers, laboratory values, demographic variables, and comorbid conditions with clinical events. Urine and serum biomarker levels, blood urea nitrogen levels, and serum leukocyte count were significantly associated with the composite clinical outcome; however, age, sex, race, and comorbid conditions were not. In multiple logistic regression analysis (shown in Table 3), levels of NGAL, serum creatinine, and blood urea nitrogen and serum leukocyte count were all predictive of poor outcome.

Identification of NGAL Expression Site

To investigate whether urinary NGAL was derived from degranulated leukocytes, we correlated NGAL with markers of neutrophils. We found a high correlation between NGAL and myeloperoxidase assayed in serum neutrophils ($R^2$=0.9; P<0.001). However, we found no correlation between urinary NGAL and urinary leukocyte counts (Spearman correlation coefficient, 0.15; P=0.060), urinary myeloperoxidase (Spearman correlation coefficient, 0.007; P=1.0), or serum leukocytes (Spearman Correlation Coefficient, −0.02; P=0.70).

In this sample of patients presenting to an inner-city emergency department, a single measurement of urinary NGAL distinguished acute kidney injury from other forms of kidney dysfunction and predicted excess morbidity after hospital admission. Logistic regression analysis demonstrated that NGAL was a better predictor of nephrology consultation, dialysis, ICU admission, and death than conventional or novel biomarkers of acute kidney injury.

In contrast to earlier studies, which utilized selected patient populations undergoing known injuries and known timepoints in a controlled manner, such as cardiothoracic surgery or introduction of known nephrotoxins, we demonstrate that the urinary NGAL level identifies acute kidney injury in a broad patient sample with different mechanisms of injury. In addition, we demonstrate that urinary NGAL level remained highly diagnostic even when the timing of injury was unknown, making NGAL a potential diagnostic of kidney disease for many clinical presentations. Interest in identifying kidney proteins that permit risk assessment, early diagnosis of injury, or surveillance of acute kidney function is intense, and a panel of biomarkers is probably required. Candidates include interleukin-18, a proinflammatory cytokine that is induced in the proximal tubule and whose levels peak 6 to 12 hours after acute disease but not chronic disease or prerenal azotemia. The urinary interleukin-18 level can increase 24 hours before the serum creatinine level in acute ischemia (AUC, 73%). The serum cystatin C level also anticipates acute kidney injury (AUC, 97%) 1 to 2 days before the serum creatinine level (AUC, 82%), and an increased urinary cystatin C level has predicted the need for dialysis (AUC, 75%) earlier than serum creatinine. However, in a study of 202 patients, cystatin C did not outperform serum creatinine in the diagnosis of acute injury or prediction of clinical outcomes. Urinary levels of kidney injury molecule-1, derived from the proximal tubule, can distinguish ischemic injury from prerenal azotemia and chronic kidney disease. In a case-control study of 20 patients with acute kidney injury and 20 control patients, kidney injury molecule-1 levels peaked 12 hours after injury (AUC, 83%) and predicted a combined end point of dialysis or death in hospitalized patients (AUC, 61%). In a cross-sectional study of 20 children, NAG identified acute kidney injury 12 hours after insult (AUC, 69%). Urinary α1-microglobulin increased 8-fold after tubular damage, and patients nearing a requirement for dialysis after acute injury also had increased urinary α1-microglobulin levels. α1-Acid glycoprotein increased 5-fold within 2 hours of cardiopulmonary surgery in patients who developed acute kidney injury.

Together, these studies demonstrate that several proteins can detect acute kidney injury early in its course, although the AUCs for these biomarkers tended to be lower than that for NGAL. In a direct comparison, NGAL was better than NAG, α1-acid glycoprotein, or α1-microglobulin at detecting acute injury and predicting clinical outcomes, even after inclusion of other biomarkers and indicators of poor outcome in a multivariate analysis.

Although biopsy is the gold standard to identify the mechanism of kidney damage, it is seldom used when the patient first presents; we used current clinical criteria to diagnose kidney disease instead. We excluded 28% of the patients because they lacked follow-up serum creatinine measurement or had end-stage kidney disease. Although we recruited patients from 6 a.m. to midnight, potentially producing a cohort biased toward medical conditions associated with acute referrals, we believe the effect to be minimal because the mean 12- to 18-hour length of stay in our emergency department allowed us to enroll admitted patients regardless of when they first presented. Finally, we studied patients from a single center, and our findings require validation in other groups of patients.

TABLE 1

Patient Characteristics by Diagnostic Group*

| Characteristic | All Patients (n = 635) | Acute Kidney Injury (n = 30) | Prerenal Azotemia (n = 88) | Stable Chronic Kidney Disease (n = 106) | Normal Kidney Function (n = 411) | P Value† |
|---|---|---|---|---|---|---|
| Mean age (SD), y | 60.1 (18.3) | 58.1 (16.7) | 65.1 (16.4) | 71.2 (14.5) | 56.3 (18.5) | <0.001 |
| Women, % | 49.0 | 53.3 | 48.9 | 42.5 | 50.4 | 0.50 |
| Black race, % | 27.1 | 36.7 | 31.8 | 33.0 | 23.8 | 0.091 |
| Mean systolic blood pressure (SD), mmHg | 131.3 (29.0) | 129 (31.1) | 114 (31.0) | 141 (29.9) | 132 (26.7) | <0.001 |
| Mean diastolic blood pressure (SD), mmHg | 74.8 (15.8) | 71.9 (18.5) | 66 (17.8) | 76 (16.3) | 76 (14.5) | <0.001 |
| Hematocrit, % | 37.2 (6.7) | 30.9 (6.6) | 35.1 (8.4) | 36.2 (6.2) | 38.3 (6.0) | <0.001 |
| Mean serum albumin level (SD), g/dL | 3.9 (1.4) | 3.3 (0.7) | 4.0 (3.3) | 3.7 (0.6) | 3.9 (0.6) | 0.039 |
| Mean blood urea nitrogen level (SD), mg/dL | 26.1 (25.3) | 72 (59.4) | 48 (32.6) | 35.4 (18.4) | 15.7 (6.6) | <0.001 |
| Mean serum leukocyte count (SD), cells × $10^9$/L | 9.7 (5.7) | 10.5 (5.3) | 11.4 (7.3) | 9.1 (4.3) | 9.4 (5.8) | 0.21 |
| Mean serum creatinine level (SD) | | | | | | <0.001 |
| Baseline | | | | | | |
| μmol/L | 106 (79.6) | 194.5 (177) | 133 (79.6) | 168 (97.2) | 79.6 (18) | |
| mg/dL | 1.2 (0.9) | 2.2 (2.0) | 1.5 (0.9) | 1.9 (1.1) | 0.8 (0.2) | |
| Emergency department presentation | | | | | | <0.001 |
| μmol/L | 124 (159) | 495 (486) | 212 (124) | 177 (133) | 79.6 (18) | |
| mg/dL | 1.4 (1.8) | 5.6 (5.5) | 2.4 (1.4) | 2.0 (1.5) | 0.9 (0.2) | |
| Change from baseline to presentation‡ | | | | | | <0.001 |
| μmol/L | 26.5 (141) | 318 (495) | 88.4 (115) | 0.884 (17.7) | 1.77 (8.84) | |
| mg/dL | 0.3 (1.6) | 3.6 (5.6) | 1.0 (1.3) | 0.01 (0.2) | 0.02 (0.1) | |
| Urine studies | | | | | | |
| Mean fractional excretion of sodium (SD), % | — | 6.9 (9.1) | 1.7 (1.9) | 3.5 (5.1) | — | <0.001 |
| Mean specific gravity (SD) | 1.014 (0.008) | 1.012 (0.006) | 1.014 (0.007) | 1.012 (0.007) | 1.015 (0.008) | <0.001 |
| Mean leukocyte count (SD), cells/HPF | 11.4 (40.7) | 37.4 (68.2) | 12.4 (29.7) | 14 (74.6) | 8.2 (25.6) | 0.052 |

TABLE 1-continued

Patient Characteristics by Diagnostic Group*

| Characteristic | All Patients (n = 635) | Acute Kidney Injury (n = 30) | Prerenal Azotemia (n = 88) | Stable Chronic Kidney Disease (n = 106) | Normal Kidney Function (n = 411) | P Value† |
|---|---|---|---|---|---|---|
| Mean erythrocyte count (SD), cells/HPF | 11.2 (47.5) | 38.1 (147) | 16.0 (44.4) | 11.4 (36.7) | 7.6 (28.8) | 0.103 |
| Biomarkers§ | | | | | | |
| Mean NGAL level (SD), μg per g creatinine | 37.6 (125) | 416 (387) | 30.1 (92.0) | 22.5 (41.1) | 15.5 (15.3) | <0.001 |
| Mean NAG level (SD), U per g creatinine | 9.2 (21.8) | 24.8 (31.7) | 11.1 (17.8) | 13.0 (18.3) | 6.7 (21.9) | <0.001 |
| Mean $\alpha_1$-microglobulin level (SD), mg per g creatinine | 29.9 (57.4) | 129 (114) | 44.5 (66.7) | 38.1 (52.1) | 17.4 (39.8) | <0.001 |
| Mean $\alpha_1$-acid glycoprotein level (SD), mg per g creatinine | 45.7 (99.5) | 201 (274) | 73.3 (103) | 32.6 (71.5) | 31.8 (65.2) | <0.001 |
| Clinical outcome | | | | | | |
| Nephrology consultation, % | 5.1 | 70.8 | 5.6 | 4.7 | 0.0 | <0.001 |
| Dialysis initiation, % | 2.0 | 30.3 | 2.8 | 2.2 | 0.0 | <0.001 |
| ICU admission, % | 6.1 | 33.4 | 13.6 | 4.7 | 2.9 | <0.001 |
| Mortality, % | 2.0 | 13.9 | 5.6 | 0.9 | 0.7 | <0.001 |

*HPF = high-powered field; NAG = N-acetyl-β-D-glucosaminidase; NGAL = neutrophil gelatinase-associated lipocalin.
†Analysis of variance was performed on log-transformed values; however, raw values are presented here.
‡Average change in creatinine was calculated only for patients whose baseline creatinine level was known.
§Values are normalized to the urinary creatinine concentration.

TABLE 2

Test Characteristics of Novel Biomarkers and Standard Diagnostic Markers*

| Biomarker and Cutoff Value | Sensitivity Value (95% CI) | Patients, n/n‡ | Specificity Value (95% CI) | Patients, n/n§ |
|---|---|---|---|---|
| NGAL | | | | |
| 85 μg/g | 0.93 (0.78-0.99) | 28/30 | 0.98 (0.97-0.99) | 594/605 |
| 130 μg/g | 0.90 (0.73-0.98) | 27/30 | 0.995 (0.99-1.00) | 602/605 |
| NAG | | | | |
| 1.0 U/g | 0.87 (0.69-0.96) | 26/30 | 0.32 (0.29-0.36); | 196/605 |
| 4.5 U/g | 0.70 (0.51-0.85) | 21/30 | 0.63 (0.59-0.67) | 383/605 |
| $\alpha_1$-Microglobulin | | | | |
| 10 mg/g | 1.00 (0.88-1.00) | 30/30 | 0.53 (0.49-0.57) | 318/604 |
| 35 mg/g | 0.80 (0.61-0.92) | 24/30 | 0.81 (0.77-0.84) | 487/604 |
| $\alpha_1$-Acid glycoprotein | | | | |
| 10 mg/g | 0.97 (0.83-1.00) | 29/30 | 0.48 (0.44-0.52) | 292/604 |
| 21 mg/g | 0.87 (0.69-0.96) | 26/30 | 0.61 (0.57-0.65) | 367/604 |
| Creatinine | | | | |
| 124 μmol/L (1.4 mg/dL) | 0.93 (0.78-0.99) | 28/30 | 0.75 (0.71-0.78) | 451/602 |
| 221 μmol/L (2.5 mg/dL) | 0.77 (0.58-0.90) | 23/30 | 0.93 (0.90-0.95) | 559/602 |
| Fractional excretion of sodium | | | | |
| 1.0% | 0.80 (0.61-0.92) | 24/30 | 0.44 (0.37-0.52) | 86/194 |

*All patient groups were used to calculate test characteristics for all markers except fractional excretion of sodium. We tested NGAL and NAG levels in 635 patients, $\alpha_1$-microglobulin and $\alpha_1$-acid glycoprotein levels in 634 patients, and creatinine levels in 632 patients. We measured fractional excretion of sodium only in the 244 patients with abnormal kidney function (acute kidney injury, chronic kidney disease, or prerenal azotemia).
AUC = area under receiver-operator characteristic curve;
NAG = N-acetyl-β-D-glucosaminidase;
NGAL = neutrophil gelatinase-associated lipocalin.
† The likelihood ratio is the ratio of posttest odds to pretest odds corresponding to a test result. As such, it indicates the effect of a test result on the odds (or, equivalently, the probability) of a disease. A very large likelihood ratio or a likelihood ratio close to zero denotes a very good test; a likelihood ratio close to 1.0 indicates a poor test. The positive likelihood ratio is the likelihood ratio after a positive test result. The negative likelihood ratio is the likelihood ratio after a negative test result.
‡Patients with acute kidney injury who tested positive/all patients with acute kidney injury.
§Patients without acute kidney injury who tested negative/all patients without acute kidney injury.

TABLE 2B

| Positive Likelihood Ratio† (95% CI) | Negative Likelihood Ratio§ (95% CI) | Positive Predictive Value | Negative Predictive Value | AUC (95% CI) |
|---|---|---|---|---|
| 51.33 (28.36-92.91) | 0.07 (0.02-0.26) | 0.737 | 0.996 | 0.948 (0.881-1.000) |
| 181.50 (58.33-564.71) | 0.10 (0.03-0.29) | 0.900 | 0.995 | |
| 1.28 (1.10-1.49) | 0.41 (0.16-1.03) | 0.059 | 0.980 | 0.713 (0.618-0.809) |
| 1.91 (1.48-2.47) | 0.47 (0.27-0.82) | 0.087 | 0.977 | |
| 2.11 (1.94-2.30) | 0 (0-0.20). | 0.095 | 1.00 | 0.887 (0.840-0.934) |
| 4.13 (3.24-5.26) | 0.25 (0.12-0.51) | 0.173 | 0.987 | |
| 1.87 (1.69-2.07) | 0.07 (0.01-0.47) | 0.087 | 0.996 | 0.832 (0.772-0.893) |
| 2.21 (1.86-2.62) | 0.22 (0.09-0.55) | 0.099 | 0.989 | |
| 3.72 (3.15-4.40) | 0.09 (0.02-0.34) | 0.187 | 0.995 | 0.921 (0.865-0.978) |
| 10.73 (7.57-15.22) | 0.25 (0.13-0.48) | 0.348 | 0.987 | |
| 1.44 (1.15-1.79) | 0.45 (0.22-0.94) | 0.162 | 0.943 | 0.708 (0.611-0.806) |

TABLE 3

Multivariate Analysis of Acute Kidney Injury Biomarker Levels Derived from Receiver-Operator Curve Analysis*

| Model Parameters | Odds Ratio (95% CI) |
|---|---|
| NGAL level (>130 µg/g) | 24.70 (7.69-79.42) |
| $\alpha_1$-Microglobulin level (>35 mg/g) | 1.85 (0.80-4.31) |
| $\alpha_1$-Acid glycoprotein level (>21 mg/g) | 0.741 (0.33-1.69) |
| NAG level (>4.5 U/g) | 1.07 (0.52-2.18) |
| Presenting creatinine level >221 µmol/L (>2.5 mg/dL) | 6.03 (2.25-16.14) |
| Blood urea nitrogen level (per mg/dL increase) | 1.01 (1.00-1.03) |
| Serum leukocyte count (per cells × $10^9$/L increase) | 1.05 (1.01-1.10) |

*Regression analysis of biomarkers as predictors of combined clinical outcomes (nephrology consultation, intensive care unit admission, dialysis initiation, or mortality).
NAG = N-acetyl-β-D-glucosaminidase;
NGAL = neutrophil gelatinase-associated lipocalin.

We claim:

1. A method for distinguishing between kidney dysfunctions in a patient having an unknown renal injury status upon admission to a medical facility, including a kidney dysfunction that presents a significant risk of progressing with time to acute renal failure, and a kidney dysfunction that does not, comprising the steps at the time of admission of the patient to the medical facility of:
    determining the level of creatinine in an isolated serum or plasma sample from a blood sample obtained from the admitted patient, to obtain a creatinine assay result;
    determining the level of NGAL in a urine sample obtained from the admitted patient to obtain a urinary NGAL assay result;
    comparing the creatinine assay result against a creatinine cutoff level; and
    comparing the urinary NGAL assay result against a urinary NGAL cutoff level,
    wherein when the urinary NGAL assay result is above the urinary NGAL cutoff level, the patient has an acute renal injury that presents a significant risk of progressing with time to acute renal failure, and when the urinary NGAL assay result is below the urinary NGAL cutoff level and the creatinine assay result is above the creatinine cutoff level, the patient has chronic kidney disease or pre-renal azotemia.

2. A method for distinguishing between kidney dysfunctions in a patient having an unknown renal injury status upon admission to a medical facility, including a kidney dysfunction that presents a significant risk of progressing with time to acute renal failure, and a kidney dysfunction that does not, comprising the steps at the time of admission of the patient to the medical facility of:
    determining the level of creatinine in an isolated serum or plasma sample from a blood sample obtained from the admitted patient to obtain a creatinine assay result;
    determining the level of NGAL in the isolated serum or plasma sample from the blood sample to obtain a circulatory NGAL assay result;
    comparing the creatinine assay result against a creatinine cutoff level; and
    comparing the circulatory NGAL assay result against a circulatory NGAL cutoff level,
    wherein when the circulatory NGAL assay result is above the circulatory NGAL cutoff level, the patient has an acute renal injury that presents a significant risk of progressing with time to acute renal failure, and when the circulatory NGAL assay result is below the circulatory NGAL cutoff level and the creatinine assay result above the creatinine cutoff level, the patient has chronic kidney disease or pre-renal azotemia.

3. The method according to claim 1 wherein the determining of the level of creatinine consists of a single measurement of serum or plasma creatinine.

4. The method according to claim 3 wherein the blood sample is a single blood sample.

5. The method according to claim 4 wherein the urine sample is obtained within 2 hours of the blood sample.

6. The method according to claim 1 wherein the urine sample is obtained at the same time as the blood sample.

7. The method according to claim 1 wherein, when the urinary NGAL assay result is above the urinary NGAL cutoff level, the mammal is prescribed at least one of a nephrology consultation, admission into intensive care, and the initiation of dialysis.

8. The method according to claim 1 wherein the urinary NGAL cutoff level is about or above 75 ng/ml urine.

9. The method according to claim 1 wherein the scrum creatinine cutoff level is at least 1 mg creatinine per dL serum.

10. The method according to claim 2 wherein the determining of the level of creatinine consists of a single measurement of serum or plasma creatinine.

11. The method according to claim 10 wherein the blood sample is a single blood sample.

12. The method according to claim 2 wherein, when the circulatory NGAL assay result is above the circulatory NGAL cutoff level, the patient is prescribed at least one of a nephrology consultation, admission into intensive care, and the initiation of dialysis.

13. The method according to claim 2 wherein the circulatory NGAL cutoff level is about or above 40 ng/ml serum.

14. The method according to claim 2 wherein the creatinine cutoff level is at least 1 mg creatinine per dL serum.

15. The method according to claim 11 wherein the determining the level of creatinine and the determining the level of NGAL are the same isolated serum or plasma sample.

16. The method according to claim 1 wherein, when the urinary NGAL assay result is below the urinary NGAL cutoff level and the creatinine assay result is above the creatinine cutoff level, if a fractional excretion of sodium is less than 1%, the patient has pre-renal azotemia.

17. The method according to claim 2 wherein, when the circulatory NGAL assay result is below the circulatory NGAL cutoff level and the creatinine assay result is above the creatinine cutoff level, if a fractional excretion of sodium is less than 1%, the patient has pre-renal azotemia.

* * * * *

UNITED STATES PATENT AND TRADEMARK OFFICE
CERTIFICATE OF CORRECTION

PATENT NO. : 7,977,110 B2
APPLICATION NO. : 12/143769
DATED : July 12, 2011
INVENTOR(S) : Jonathan M. Barasch et al.

Page 1 of 1

It is certified that error appears in the above-identified patent and that said Letters Patent is hereby corrected as shown below:

In the Specifications:

Col. 1, Line 3 insert

--GOVERNMENT RIGHTS
This invention was made with government support under DK053289, DK052612, DK070163, DK055388, and DK058872 awarded by the National Institutes of Health. The government has certain rights in the invention.--

Signed and Sealed this
Twenty-third Day of April, 2013

Teresa Stanek Rea
*Acting Director of the United States Patent and Trademark Office*